United States Patent
Pieper et al.

[11] Patent Number: 5,393,774
[45] Date of Patent: Feb. 28, 1995

[54] PHENYLETHANOLAMINES, PHARMACEUTICAL COMPOSITIONS CONTAINING THESE COMPOUNDS AND PROCESS FOR PREPARING THEM

[76] Inventors: Helmut Pieper, Kapellenweg 5; Günther Engelhardt, Unterer Bühl 18, both of W-7950 Biberach 1, Germany

[21] Appl. No.: 187,671

[22] Filed: Jan. 27, 1994

Related U.S. Application Data

[63] Continuation of Ser. No. 855,026, Jul. 14, 1992, abandoned.

[30] Foreign Application Priority Data

Sep. 7, 1990 [DE] Germany .................. 4028398
Sep. 3, 1991 [WO] WIPO .............. PCT/EP91/01658

[51] Int. Cl.⁶ ............... A61K 31/275; C07C 28/58; C07C 255/50; C07D 317/54
[52] U.S. Cl. .................... 514/452; 514/464; 514/522; 514/524; 549/362; 549/440; 558/416; 558/418
[58] Field of Search .......... 558/418, 416; 549/362, 549/440; 514/522, 524, 452, 464

[56] References Cited

U.S. PATENT DOCUMENTS

| | | | |
|---|---|---|---|
| 4,119,710 | 10/1978 | Engelhardt et al. | 558/419 X |
| 4,845,262 | 7/1989 | Lindel et al. | 558/145 |
| 4,943,591 | 7/1990 | Skidmore et al. | 544/398 X |
| 5,232,946 | 8/1993 | Hurhaus et al. | 514/546 |

FOREIGN PATENT DOCUMENTS

| | | | |
|---|---|---|---|
| 0057900 | 8/1982 | European Pat. Off. | |
| 2088873 | 6/1982 | United Kingdom | 558/418 |

*Primary Examiner*—Joseph Paul Brust
*Attorney, Agent, or Firm*—D. E. Frankhouser; A. R. Stempel; M-E. M. Timbers

[57] ABSTRACT

The invention relates to phenylethanolamines of general formula

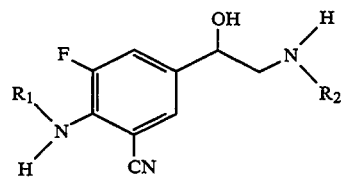

wherein $R_1$ and $R_2$ are defined as in claim 1, the enantiomers and the acid addition salts thereof, which have valuable pharmacological properties, not only analgesic, antiphlogistic, broncholytic, uterus-spasmolytic, lipolytic effects and an antispastic effect on the cross-striped muscle, but also $\beta_2$-mimetic and/or $\beta_1$-blocking effects, the use thereof as pharmaceuticals and as performance enhancers and processes for preparing them.

6 Claims, No Drawings

PHENYLETHANOLAMINES, PHARMACEUTICAL COMPOSITIONS CONTAINING THESE COMPOUNDS AND PROCESS FOR PREPARING THEM

This is a continuation of application Ser. No. 07/855,026, filed Jul. 14, 1992.

The present invention relates to phenylethanolamines of general formula

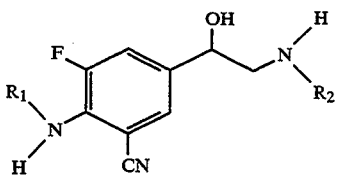

the enantiomers and acid addition salts thereof, particularly for pharmaceutical use the physiologically acceptable acid addition salts thereof with inorganic or organic acids, the use thereof as pharmaceuticals and as performance enhancers and processes for preparing them.

The new compounds have valuable pharmacological properties: in addition to analgesic, antiphlogistic, broncholytic, uterus-spasmolytic, lipolytic and anti-spastic effects on the cross-striped musculature, they also have $\beta_2$-mimetic and/or $\beta_1$-blocking effects. They may also be used as performance enhancers.

In general formula I above $R_1$ represents a hydrogen atom or an alkoxycarbonyl group having a total of 2 to 5 carbon atoms and $R_2$ represents a group of the formula

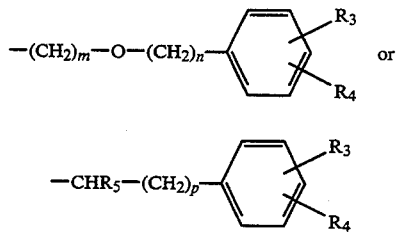

wherein
 m represents the numbers 2 to 8,
 n represents the numbers 1 to 7,
 p represents the numbers 1 to 3,
 $R_3$ and $R_4$, which may be identical or different, represent hydrogen, fluorine, chlorine or bromine atoms, methyl, ethyl, hydroxy, methoxy or ethoxy groups or
 $R_3$ and $R_4$ together represent a methylenedioxy or ethylenedioxy group and
 $R_5$ represents a hydrogen atom or a methyl or ethyl group.

For example, the groups $R_1$ and $R_2$ defined above may have the following meanings:

$R_1$ may be a hydrogen atom, a methoxycarbonyl, ethoxycarbonyl, n-propoxycarbonyl isopropoxycarbonyl, n-butoxycarbonyl, 1-methyl-n-propoxycarbonyl or 2-methyl-n-propoxycarbonyl group and $R_2$ may represent a 2-phenyl-ethyl, 3-phenyl-propyl, 4-phenyl-butyl, 2-phenyl-1-methylethyl, 3-phenyl-1-methyl-propyl, 4-phenyl-1-methyl-butyl, 2-phenyl-1-ethyl-ethyl, 3-phenyl-1-ethyl-propyl, 4-phenyl-1-ethyl-butyl, 2-(4-methoxyphenyl)-ethyl, 3-(4-methoxyphenyl)-propyl, 4-(4-methoxyphenyl)-butyl, 2-(4-methoxyphenyl)-1-methylethyl, 3-(4-methoxyphenyl)-1-methyl-propyl, 4-(4-methoxyphenyl)-1-methyl-butyl, 2-(4-methoxyphenyl)-1-ethyl-ethyl, 3-(4-methoxyphenyl)-1-ethyl-propyl, 4-(4methoxyphenyl)-1-ethyl-butyl, 2-(4-chlorophenyl)-ethyl, 3-(4-chlorophenyl)-propyl, 4-(4-chlorophenyl)-butyl, 2-(4-chlorophenyl)-1-methyl-ethyl, 3-(4-chlorophenyl)-1-methylpropyl, 4-(4-chlorophenyl)-1-methyl-butyl, 2-(4-chlorophenyl)-1-ethyl-ethyl, 3-(4-chlorophenyl)-1-ethyl-propyl, 4-(4-chlorophenyl)-1-ethyl-butyl, 2-benzyloxy-ethyl, 2-(2-phenylethoxy)-ethyl, 2-(3-phenyl-propoxy)-ethyl, 2-(4-phenylbutoxy)-ethyl, 2-(5-phenylpentoxy)-ethyl, 2-(6-phenylhexoxy)-ethyl, 2-(7-phenylheptoxy)-ethyl, 2-(4-methoxybenzyloxy)-ethyl, 2-[2-(4-methoxyphenyl)-ethoxy]-ethyl, 2-[3-(4-methoxyphenyl)-propoxy]-ethyl, 2-[4-(4-methoxyphenyl)-butoxy]-ethyl, 2-[5-(4-methoxyphenyl)-pentoxy]-ethyl, 2-[6-(4-methoxyphenyl)-hexoxy]-ethyl, 2-[7-(4-methoxyphenyl)-heptoxy]-ethyl, 3-benzyloxy-propyl, 3-(2-phenylethoxy)-propyl, 3-(3-phenylpropoxy)-propyl, 3-(4-phenylbutoxy)-propyl, 3-(5-phenylpentoxy)-propyl, 3-(6-phenylhexoxy)-propyl, 3-(7-phenylheptoxy)-propyl, 3-(4-methoxybenzyloxy)-propyl, 3-[2-(4-methoxyphenyl)-ethoxy]-propyl, 3-[3-(4-methoxyphenyl)-propoxy]-propyl, 3-[4-(4-methoxyphenyl)-butoxy]-propyl, 3-[5-(4-methoxyphenyl)-pentoxy]-propyl, 3-[6-(4-methoxyphenyl)-hexoxy]-propyl, 3-[7-(4-methoxyphenyl)-heptoxy]-propyl, 4-benzyloxybutyl, 4-(2-phenylethoxy)-butyl, 4-(3-phenylpropoxy)-butyl, 4-(4-phenylbutoxy)-butyl, 4-(5-phenylpentoxy)-butyl, 4-(6-phenylhexoxy)-butyl, 4-(7-phenylheptoxy)-butyl, 4-(4-methoxybenzyloxy)-butyl, 4-[2-(4-methoxyphenyl)-ethoxy]butyl, 4-[3-(4-methoxyphenyl)-propoxy]-butyl, 4-[4-(4-methoxyphenyl)-butoxy]-butyl, 4-[5-(4-methoxyphenyl)-pentoxy]-butyl, 4-[6-(4-methoxyphenyl)-hexoxy]-butyl, 4-[7-(4- methoxyphenyl)-heptoxy]-butyl, 5-benzyloxy-pentyl, 5-(2-phenylethoxy)-pentyl, 5-(3-phenylpropoxy)-pentyl, 5-(4-phenylbutoxy)-pentyl, 5-(5-phenylpentoxy)-pentyl, 5-(6-phenylhexoxy)-pentyl, 5-(7-phenylheptoxy)-pentyl, 5-(4-methoxybenzyloxy)-pentyl, 5-[2-(4-methoxyphenyl)-ethoxy]-pentyl, 5-[3-(4-methoxyphenyl)-propoxy]-pentyl, 5-[4-(4-methoxyphenyl)-butoxy]-pentyl, 5-[5-(4-methoxyphenyl)-pentoxy]-pentyl, 5-[6-(4-methoxyphenyl)-hexoxy]-pentyl, 5-[7-(4-methoxyphenyl)-heptoxy]-pentyl, 6-benzyloxyhexyl, 6-(2-phenylethoxy)-hexyl, 6-(3-phenylpropoxy)-hexyl, 6-(4-phenylbutoxy)-hexyl, 6-(5-phenylpentoxy)-hexyl, 6-(6-phenylhexoxy)-hexyl, 6-(7-phenylheptoxy)-hexyl, 6-(4-methoxybenzyloxy)-hexyl, 6-[2-(4-methoxyphenyl)-ethoxy]-hexyl, 6-[3-(4-methoxyphenyl)-propoxy]-hexyl, 6-[4-(4-methoxyphenyl)-butoxy]-hexyl, 6-[5-(4-methoxyphenyl)-pentoxy]-hexyl, 6-[6-(4-methoxyphenyl)-hexoxy]-hexyl, 6-[7-(4-methoxyphenyl)-heptoxy]-hexyl, 7-benzyloxy-heptyl, 7-(2-phenylethoxy)-heptyl, 7-(3-phenylpropoxy)-heptyl, 7-(4-phenylbutoxy)-heptyl, 7-(5-phenylpentoxy)-heptyl, 7-(6-phenylhexoxy)-heptyl, 7-(7-phenylheptoxy)-heptyl, 7-(4-methoxybenzyloxy)-heptyl, 7-[2-(4-methoxyphenyl)-ethoxy]-heptyl, 7-[3-(4-methoxyphenyl)-propoxy]-heptyl, 7-[4-(4-methoxyphenyl)-butoxy]-heptyl, 7-[5-(4-methoxyphenyl)-pentoxy]-heptyl, 7-[6-(4-methoxyphenyl)-hexoxy]-heptyl, 7-[7-(4-methoxyphenyl)-heptoxy]-heptyl, 2-(4-chlorobenzyloxy)-ethyl, 2-[2-(4-chlorophenyl)-ethoxy]-ethyl, 2-[3-(4-chlorophenyl)propoxy]-ethyl, 2-[4-(4- chlorophenyl)-butoxy]-ethyl, 2-[5-(4-chlorophenyl)-pentoxy]ethyl, 2-[6-(4-chlorophenyl)-hexoxy]-ethyl, 2-[7-(4-chlorophenyl)-heptoxy]-ethyl, 3-(4-chlorobenzyloxy)-propyl, 3-[2-(4-chlorophenyl)-ethoxy]-propyl, 3-[3-(4-chlorophenyl)propoxy]-propyl, 3-[4-(4-chlorophenyl)-butoxy]-propyl, 3-[5-(4-chlorophenyl)-pentoxy]propyl, 3-[6-(4-chlorophenyl)-hexoxy]-propyl, 3-[7-(4-chlorophenyl)-heptoxy]-propyl, 4-(4-chlorobenzyloxy)-butyl, 4-[2-(4-chlorophenyl)-ethoxy]-butyl, 4-[3-(4-chlorophenyl)propoxy]-butyl, 4-[4-(4-chlorophenyl)-butoxy]-butyl, 4-[5-(4-chlorophenyl)-pentoxy]-butyl, 4-[6-(4-chlorophenyl)-hexoxy]-butyl, 4-[7-(4-chlorophenyl)-heptoxy]-butyl, 5-(4-chlorobenzyloxy)-pentyl, 5-[2-(4-chlorophenyl)-ethoxy]-pentyl, 5-[3-(4-chlorophenyl)propoxy]-pentyl, 5-[4-(4-chlorophenyl)-butoxy]-pentyl, 5-[5-(4-chlorophenyl)-pentoxy]pentyl, 5-[6-(4-chlorophenyl)-hexoxy]-pentyl, 5-[7-(4-chlorophenyl)-heptoxy]-pentyl, 6-(4-chlorobenzyloxy)-hexyl, 6-[2-(4-chlorophenyl)-ethoxy]-hexyl, 6-[3-(4-chlorophenyl)propoxy]-hexyl, 6-[4-(4-chlorophenyl)-butoxy]-hexyl, 6-[5-(4-chlorophenyl)-pentoxy]hexyl, 6-[6-(4-chlorophenyl)-hexoxy]-hexyl, 6-[7-(4-chlorophenyl)-heptoxy]-hexyl, 7-(4-chlorobenzyloxy)-heptyl, 7-[2-(4-chlorophenyl)-ethoxy]-heptyl, 7-[3-(4-chlorophenyl)-propoxy]-heptyl, 7-[4-(4-chlorophenyl)-butoxy]-heptyl, 7-[5-(4-chlorophenyl)-pentoxy]heptyl, 7-[6-(4-chlorophenyl)-hexoxy]-heptyl, 7-[7-(4-chlorophenyl)-heptoxy]-heptyl, 2-(4-hydroxyphenyl)-ethyl, 3-(4-hydroxyphenyl)-propyl, 4-(4-hydroxyphenyl)-butyl, 2-(4-hydroxyphenyl)-1-methyl-ethyl, 3-(4-methoxyphenyl)-1-methyl-propyl, 4-(4-hydroxyphenyl)-1-methyl-butyl, 2-(4-hydroxyphenyl)-1-ethyl-ethyl, 3-(4-hydroxyphenyl)-1-ethyl-propyl or 4-(4-hydroxyphenyl)-1-ethyl-butyl group.

Preferred compounds of general formula I above are those wherein $R_1$ represents a hydrogen atom, a methoxycarbonyl or ethoxycarbonyl group, m represents the number 5, 6 or 7, n represents the number 3, 4 or 5, p represents the number 1 or 2, $R_3$ represents a hydrogen atom or a hydroxy or methoxy group, $R_4$ represents a hydrogen atom and $R_5$ represents a methyl group, the enantiomers and the acid addition salts thereof.

According to the invention, the new compounds of general formula I above may be prepared by the following process:

Reduction of an aldehyde of general formula

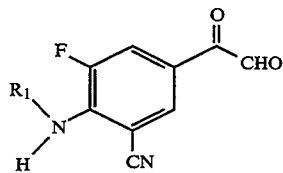

(wherein
  $R_1$ is defined as hereinbefore) or a hydrate thereof, in the presence of an amine of general formula

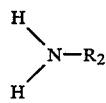   (III)

wherein
  $R_2$ is defined as hereinbefore.

The reduction is carried out in a solvent such as methanol, ethanol, butanol, diethylether, tetrahydrofuran or dioxane with a complex metal hydride or with catalytically activated hydrogen at temperatures between $-20°$ C. and the boiling temperature of the solvent used.

Appropriately, the reduction is carried out with a complex metal hydride such as sodium borohydride or lithium aluminum hydride in a suitable solvent such as methanol, methanol/water, diethylether or tetrahydrofuran at temperatures between $-20°$ C. and the boiling temperature of the solvent used, e.g. at temperatures between $0°$ and $50°$ C., and the reduction with catalytically activated hydrogen is carried out in the presence of a catalyst such as platinum, palladium, Raney nickel or Raney cobalt at temperatures between $0°$ and $100°$ C., preferably at ambient temperature, and under a hydrogen pressure of 1 to 5 atmospheres.

The reaction is expediently carried out without isolating the compound of general formula

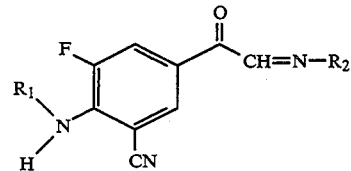

formed in situ, in which $R_1$ and $R_2$ are defined as hereinbefore, but this compound may, of course, be isolated and reduced in accordance with the process described above.

The new compounds of general formula I obtained may subsequently, if desired, be resolved into their enantiomers, preferably by fractional crystallization of a mixture of the diastereomeric salts thereof with an optically active acid, e.g. D(−)-tartaric acid, L(+)-tartaric acid, dibenzoyl-D-tartaric acid, dibenzoyl-L-tartaric acid, (−)-camphor-10-sulphonic acid, (+)-camphor-10-sulphonic acid, L(−)-malic acid, D(−)-mandelic acid, L(+)-mandelic acid, d-α-bromo-camphor-π-sulphonic acid or D(−)-quinic acid. However, the racemate cleaving may also be carried out by column chromatography on an optically active carrier material, e.g. acetyl cellulose.

Furthermore, the racemate cleaving may also be effected by resolving a mixture of diastereomeric compounds which is obtained by reacting a compound of general formula I with a chiral compound, e.g. with a chiral acyl group such as an N-protected amino acid, a chiral hemiester of carbonic acid, a chiral carboxylic acid or a chiral isocyanate, and subsequent cleaving of the chiral adjuvant. Diastereomeric compounds of this kind are preferably resolved by fractional crystallization or by chromatography on an inert carrier and the subsequent cleaving of the chiral adjuvant is expediently effected by hydrolysis or solvolysis.

Furthermore, the new compounds of general formula I obtained may, if desired, be converted with inorganic or organic acids into the physiologically acceptable acid addition salts thereof with 1 equivalent of the acid in question. Suitable acids include, for example, hydrochloric, hydrobromic, sulphuric, phosphoric, lactic, citric, tartaric, maleic or fumaric acid.

The compounds of general formulae II and III used as starting materials may be prepared by methods known per se. Thus, for example, a compound of general formula II is obtained by oxidation of a corresponding acetophenone with selenium dioxide (see the Examples), with no need to isolate the starting compounds required.

As already mentioned hereinbefore, the new compounds of the present application and the physiologically acceptable salts thereof with inorganic and organic, acids have valuable pharmacological properties as well as being well absorbed by the oral route; in addition to analgesic, antiphlogistic, broncholytic, uterus-spasmolytic, lipolytic and antispastic effects on the cross-striped musculature, they also have $\beta_2$-mimetic and/or $\beta_1$-blocking effects and are particularly characterized by the rapid onset of their effect after oral administration and a long duration of activity.

By way of example, the following substances:
A = 1-(4-ethoxycarbonylamino-3-cyano-5-fluoro-phenyl)-2-[6-(4-phenyl-butoxy)hexylamino]-ethanol-hydrochloride,
B = 1-(4-amino-3-cyano-5-fluoro-phenyl)-2-[6-(4-phenylbutoxy)-hexyl-amino]ethanol-hydrochloride and
C = 1-(4-amino-3-cyano-5-fluoro-phenyl)-2-[2-(4-methoxyphenyl)-1-methyl-ethylamino]-ethanol-hydrochloride were investigated by comparison with
V = 1-(4-amino-3,5-dichloro-phenyl)-2-[6-(4-phenyl-butoxy)-hexylamino]-ethanolhydrochloride (see EP-A-181709) for their broncholytic effects:

The broncholytic effect was investigated by the test arrangement according to KONZETT and RÖSSLER (Arch. exp. Path. Pharmak. 195, 71 (1940)) on anesthetized guinea-pigs. An $ED_{50}$ was calculated from the average percentage reduction, achieved with the various intravenous doses, in the bronchospasm triggered by intravenous administration of 20 µg/kg of acetylcholine, by linear regression analysis according to LINDER (Statistische Methoden, 4th Edition, pp. 148–162, Birkhäuser, Basel 1964):

| Substance | after i.v. administration $ED_{50}$ µg/kg |
|---|---|
| A | 10.20 |
| B | 2.50 |
| C | 0.16 |
| V | >400 |

The new compounds of the general formula are well tolerated and when compounds A to C were administered in doses of 400 µg/kg i.v. to guinea-pigs, for example, no toxic side effects were observed.

The compounds of general formula I prepared according to the invention and the physiologically acceptable salts thereof with inorganic or organic acids are therefore suitable for tocolysis, for lowering blood pressure by peripheral vasodilation, for mobilizing body fat or treating allergic conditions such as allergic asthma or allergic inflammatory conditions, spastic diseases of the respiratory tract, of various origins, or heart rhythm disorders, and for this purpose optionally in conjunction with other active substances, they may be incorporated in conventional pharmaceutical preparations such as plain or coated tablets, solutions, sprays, ampoules or suppositories. The single dose in humans is 1 to 50 µg, preferably 2.5 to 25 µg, once or twice a day.

Furthermore, the new compounds of general formula I and the acid addition salts thereof may be used to treat obese animals such as dogs and, as a consequence of their body fat-reducing (lipolytic) effect, for reducing undesirable fat deposits in animal husbandry, i.e. for improving the meat quality of agricultural animals such as pigs, cattle, sheep and poultry. In animals, the above-mentioned compounds may be administered by oral or non-oral route, e.g. as a feed additive or by injection or by means of implanted minipumps. The daily dose is between 0.01 and 100 µg/kg, preferably between 0.01 to 10 µg/kg of body weight.

Moreover, the new compounds of general formula I and the acid addition salts thereof may be used as performance enhancers in animals for promoting and accelerating growth, milk and wool production and for improving the utilization of fodder, the quality of the carcass and for shifting the ratio of meat to fat in favor of meat. The active substances are used in agricultural, breeding, ornamental and pet animals.

Animals used for agricultural and breeding purposes include mammals such as cattle, pigs, horses, sheep, goats, rabbits, hares, deer, animals kept for fur such as mink, chinchilla, poultry such as hens, geese, ducks, turkeys, fish, e.g. carp, trout, salmon, eels, tench, pike and reptiles such as snakes and crocodiles.

Ornamental and pet animals include mammals such as dogs and cats, birds such as parrots, canaries, and fish such as ornamental and aquarium fish, e.g. goldfish.

The active substances are used throughout all the growth and performance phases of the animals, irrespective of their sex. Preferably, the active substances are used during the intensive period of growth and performance. Depending on the type of animal, this intensive phase of growth and performance lasts from one month to 10 years.

The quantity of active substances administered to the animals in order to achieve the desired effect can be varied substantially, on account of the favorable properties of the active substances. The dosage is preferably 0.01 to 50 µg/kg, more particularly 0.01 to 25 µg/kg of body weight per day. A suitable quantity of active substance and the correct duration of administration will depend particularly on the type of animal, its age, sex, state of health and the method of keeping and feeding the animals and can readily be determined by anyone skilled in the art.

The active substances are administered to the animals by conventional methods. The method of administration will depend particularly on the type of animal, its behavior and state of health.

The active substances may be administered in one go. However, the active substances may also be administered temporarily or continuously throughout all or part of the growth phase. In the case of continuous administration, the substances may be given once or several times a day at regular or irregular intervals.

The substances are administered by oral or parenteral route in suitable formulations or in pure form. Oral formulations include powders, tablets, granules, drenches, boli and feeds, premixes for feeds and formulations for administering in drinking water.

The oral preparations contain the active substance in concentrations of 0.01 ppb–100%, preferably 0.01 ppb–10%.

Parenteral formulations are injections in the form of solutions, emulsions and suspensions, as well as implants.

The active substances may be present in the formulations on their own or in admixture with other active substances, mineral salts, trace elements, vitamins, protein substances, colorings, fats or flavorings.

The concentration of active substances in the finished fodder is normally about 0.01 ppb–50 ppm, preferably 0.1 ppb–10 ppm.

The active substances may be added to the feed as they are or in the form of premixes or feed concentrates.

Thus, the feedstuffs according to the invention contain, in addition to the active substance and possibly a conventional vitamin-mineral mixture, for example: barley, low-grade wheat flour, broad beans, shredded rape extract and edible fat for fattening pigs; maize, soya-bean flour, meat meal, edible fat and soya oil for broilers; shredded sugar beet, maize gluten, malted germs, soya-bean flour, wheat and molasses for cattle; and barley, soya-bean flour, maize and molasses for lambs. One of the above-mentioned compounds of formula I is added to this fodder as active substance in a concentration of 0.01 ppb to 0.50%, preferably from 0.1 ppb to 0.05%, the mixing preferably being effected by producing a premix of the active substance. The content in this premix is, for example, 5 to 10,000 mg, preferably 50 to 1,000 mg, appropriately in 1,000 g of corn starch.

The Examples which follow are intended to illustrate the invention:

Example A 6-(4-Phenylbutoxy)-hexylamine

A solution of 46.6 g (0.15 mol) of 6-(4-phenylbutoxy)-hexyl-bromide and 27.6 g (0.15 mol) of potassium phthalimide in 400 ml of acetone is refluxed for 70 hours. After cooling, the potassium bromide precipitated is removed by suction filtering and the solvent is distilled off in vacuo. The oily residue thus obtained, consisting of crude 6-(4-phenyl-butoxy)-N-hexyl-phthalimide, is stirred into 300 ml of dichloromethane and 300 ml of 40% methylamine solution overnight. The organic phase is separated off and the aqueous phase is extracted twice more with dichloromethane. The combined organic phases are dried over sodium sulphate and evaporated down in vacuo. The oily residue is dissolved in ether, the solids precipitated are filtered off and the filtrate is evaporated to dryness. The colorless oil remaining is distilled. $Bp_{0.2} = 143°–145°$ C.

Example B 2-(4-Methoxyphenyl)-1-methyl-ethylamine

A solution of 32 g (0.21 mol) of 4'-methoxyacetophenone and 165 g (2.1 mol) of ammonium acetate in 450 ml of methanol is combined with 13.5 g (0.21 mol) of sodium cyanoborohydride, which is added in batches thereto at ambient temperature, with stirring. After a further 20 hours, ice is added and the mixture is acidified with hydrochloric acid (conc. HCl $H_2O = 1/1$) until the pH is 2. The acidic solution is extracted with dichloromethane. The aqueous phase is then mixed with conc. ammonia, with cooling, until a clearly alkaline reaction occurs and then extracted exhaustively with dichloromethane. The combined dichloromethane extracts are dried over sodium sulphate and evaporated to dryness in vacuo. The crude 2-(4-methoxyphenyl)-1-methylethylamine thus obtained is purified by column chromatography over silica gel (eluant: dichloro-methane/methanol = 20/1) to remove any by-products. A colorless oil is obtained which can be used for reaction without any further purification.

Example 1

1-(4-Ethoxycarbonylamino-3-cyano-5-fluoro-phenyl)-2-[6-(4-phenyl-butoxy)hexylamino]-ethanol-hydrochloride At 60 20 C., with stirring, 5 g (0.02 mol) of 4'-ethoxycarbonylamino-3'-cyano-5'-fluoro-acetophenone and 1.5 g of kieselguhr are added to a solution of 2.4 g of selenium dioxide in 50 ml of dioxane and 3 ml of water. The mixture is then refluxed for 4 hours and then filtered to remove solids. After cooling, 7 g (0.025 mol) of 6-(4-phenylbutoxy)-hexylamine, dissolved in a little dioxane, are added to the resulting solution of 4'-ethoxycarbonylamino-3'-cyano-5'-fluoro-phenylglyoxal. After the mixture has stood for one hour at ambient temperature it is diluted with 100 ml of ethanol and 3 g of sodium borohydride are added, with stirring and cooling. It is left to stand overnight at ambient temperature, any excess sodium borohydride is destroyed with acetone and the mixture is then evaporated to dryness in vacuo. The solid residue is distributed between water and dichloromethane and any undissolved matter is removed by suction filtering using kieselguhr. The filter cake is washed three times more with dichloromethane. The combined dichloromethane solutions are dried and evaporated to dryness in vacuo. The solid residue is purified by chromatography over silica gel, using dichloromethane/methanol = 20/1 and 8/1 as eluant. The residue obtained after evaporation is dissolved in ethanol. This solution is acidified up to a pH of 3 using ethereal hydrochloric acid. After the addition of ether, crystallization occurs.

Melting point: 119°–123° C.

Example 2

1-(4-Amino-3-cyano-5-fluoro-phenyl)-2-[6-(4-phenyl-butoxy)-hexylamino]-ethanolhydrochloride Prepared analogously to Example 1, starting from 4'-amino-3'-cyano-5'-fluoroacetophenone and 6-(4-phenylbutoxy)-hexylamine. Melting point: 173°–176° C.

Example 3

1-(4-Ethoxycarbonylamino-3-cyano-5-fluoro-phenyl)-2-[2-(4-methoxyphenyl)-1-methylethylamino]-ethanol-hydrochloride Prepared analogously to Example 1, starting from 4'-ethoxycarbonylamino-3'-cyano-5'-fluoro-acetophenone and 2-(4-methoxyphenyl)-1-methyl-ethylamine. Melting point: 123°–125° C. cl Example 4

1(4-Amino-3-cyano-5-fluoro-phenyl)-2-[2-(4-methoxyphenyl)-1-methyl-ethylamino]ethanol-hydrochloride Prepared analogously to Example 1, starting from 4'-amino-3'-cyano-5'-fluoroacetophenone and 2-(4-methoxyphenyl)-1-methyl-ethylamine. Melting point: 156°–158° C.

Example 5

Tablets containing 5 μg of
1-(4-ethoxycarbonylamino-3-cyano-5-fluoro-phenyl)-2-
[6-(4phenyl-butoxy)-hexylamino]-ethanol-hydrochloride

| Composition 1 tablet contains: | |
|---|---|
| Active substance | 0.005 mg |
| Lactose | 82.495 mg |
| Potato starch | 33.000 mg |
| Polyvinylpyrrolidone | 4.000 mg |
| Magnesium stearate | 0.500 mg |
| | 120.000 mg |

Method of preparation

The active substance and polyvinylpyrrolidone are dissolved in ethanol. The mixture of lactose and potato starch is evenly moistened with the active substance/granulating solution. Moist screening is carried out using a 1.5 mm mesh. It is then dried at 50° C. and dry screening is carried out with a 1.0 mm mesh. The resulting granules are mixed with magnesium stearate and compressed to form tablets.
Weight of tablet: 120 mg
Punch: 7 mm, flat

Example 6

Coated tablets containing 10 μg of
1-(4-ethoxy-carbonylamino-3-cyano-5-fluorophenyl)-2-
]2-(4-methoxyphenyl)-1-methyl-ethylamino]-ethanol-hydrochloride

| Composition 1 tablet contains: | |
|---|---|
| Active substance | 0.010 mg |
| Lactose | 82.490 mg |
| Potato starch | 33.000 mg |
| Polyvinylpyrrolidone | 4.000 mg |
| Magnesium stearate | 0.500 mg |
| | 120.000 mg |

Method of preparation

Coated tablet cores are produced analogously to the tablets in Example 5.
Weight of core: 120 mg
Punch: 7 mm, convex
The cores are coated, by the known method with a coating consisting essentially of sugar and talc. The finished coated tablets are polished with beeswax.
Weight of coated tablet: 200.0 mg

Example 7

Oblong gelatin capsules containing 5 μg of
1-(4-ethoxycarbonylamino-3-cyano-5fluoro-phenyl)-2-
[6-(4-phenyl-butoxy)-hexylamino]-ethanol-hydrochloride

| Composition 1 tablet contains: | |
|---|---|
| Active substance | 0.005 mg |
| Lactose | 59.995 mg |
| Corn starch | 60.000 mg | continued

| Composition 1 tablet contains: | |
|---|---|
| | 120.000 mg |

Method of preparation

The active substance is thoroughly mixed with lactose and corn starch and packed into oblong gelatin capsules of a suitable size.
Capsule contents: 120.0 mg

Example 8

Ampoules contain 2 82 g of
1-(4-amino-3-cyano-5-fluoro-phenyl)-2-[6-(4-phenyl-butoxy)hexyl-amino]-ethanol-hydrochloride per 2 ml

| Composition 1 ampoule contains: | |
|---|---|
| Active substance | 0.002 mg |
| Citric acid | 2.500 mg |
| Sodium hydrogen phosphate | 7.500 mg |
| Common salt | 4.600 mg |
| Ampoule water ad | 2.000 ml |

Method of preparation

The active substance, buffer substances and common salt are dissolved in the ampoule water and then filtered to remove any pathogens.
Packaging: in brown 2 ml ampoules under protective gas (N₂) Sterilization: 20 minutes at 120° C.

Example 9

Suppositories containing 5 μg of
1-(4-ethoxycarbonyl-amino-3-cyano-5-fluoro-phenyl)2-
[2-(4-methoxyphenyl)-1-methyl-ethylamino]-ethanol-hydrochloride

| Composition 1 suppository contains: | |
|---|---|
| Active substance | 0.005 mg |
| Suppository mass (e.g. Witepsol W 45 | 1699.995 mg |
| | 1700.000 mg |

Method of preparation

The finely powdered active substance is stirred into the molten suppository mass cooled to 40° C., using an immersion homogenizer, and at 37° C. the mass is poured into slightly chilled molds.
Weight of suppository: 1.7 g

Example 10

Syrup containing 2 μg of
1-(4-ethoxycarbonylamino-3-cyano-5-fluoro-phenyl)-2-
[6-(4-phenyl-butoxy)-hexylamino]-ethanol-hydrochloride per 5 ml

| Composition 100 ml of syrup contain: | |
|---|---|
| Active substance | 0.04 mg |
| Benzoic acid | 0.10 g |

-continued

| Composition | |
|---|---|
| 100 ml of syrup contain: | |
| Tartaric acid | 1.00 g |
| Sugar | 50.00 g |
| Orange flavoring | 1.00 g |
| Red food coloring | 0.05 g |
| Distilled water ad | 100.00 ml |

Method of preparation

About 60 g of distilled water are heated to 80° C. and benzoic acid, tartaric acid, active substance, coloring and sugar are dissolved successively therein. After cooling to ambient temperature, the flavoring is added and the mixture is made up to the required volume. The syrup is filtered.

Example 11

Aerosol spray containing 1 μg of 1-(4-amino-3-cyano-5-fluoro-phenyl)-2-[2-(4-methoxyphenyl)-1-methyl-ethylamino]-ethanol-hydrochloride per actuation

| Composition | |
|---|---|
| Active substance | 0.00025 mg |
| Soya lecithin | 0.05000 mg |
| Propellant gas mixture | 69.94975 mg |
| 11/12/114 (23:54:23) | |
| | 70.00000 mg |

Example 12

Aerosol spray containing 1 μg of 1-(4-amino-3-cyano-5-fluoro-phenyl)-2-[6-(4-Phenyl-butoxy)-hexyl-amino]-ethanol-hydrochloride per actuation

| Composition | |
|---|---|
| Active substance | 0.00025 mg |
| 99.9% pure ethanol | 0.87500 mg |
| Propellant gas mixture | 69.12475 mg |
| 11/12/114 (23:54:23) | |
| | 70.00000 mg |

Example 13

Inhalant solution containing 59 mg of 1-(4-amino-3-cyano-3-fluoro-phenyl)-2-[6-(4-phenyl-butoxy)-hexylamino]-ethanol hydrochloride per 100 ml

| Composition | |
|---|---|
| Active substance | 0.59 mg |
| Sodium chloride | 900.00 mg |
| Benzalkonium chloride | 25.00 mg |
| Distilled water ad | 100.00 ml |

Method of preparation

The active substance, common salt and benzalkonium chloride are dissolved in distilled water and then filtered to remove any pathogens.

Example 14

Complete feed II for fattening pigs

| | |
|---|---|
| Barley | 379 g/kg |
| Low-grade wheat flour | 200 g/kg |
| Manioc flour | 135 g/kg |
| Broad beans | 100 g/kg |
| Shredded rape extract | 100 g/kg |
| Edible fat | 65 g/kg |
| Lysine-rich mineral feed for pigs | 20 g/kg |
| Active substance premix | 1 g/kg |

These components, carefully mixed in the amounts specified, produce 1 kg of feed.

The 1 g of active substance premix contains, for example, 2 mg of a compound according to the invention and 0.998 g of corn starch.

Example 15

Fattening feed II for broilers

| | |
|---|---|
| Maize | 634 g/kg |
| Soya bean flour | 260 g/kg |
| Meat meal | 40 g/kg |
| Edible fat | 25 g/kg |
| Soya oil | 17 g/kg |
| Bicalcium phosphate | 12 g/kg |
| Calcium carbonate | 6 g/kg |
| Vitamin/mineral mixture | 5 g/kg |
| Active substance premix | 1 g/kg |

These components, when carefully mixed in the quantities specified, produce 1 kg of feed.

The 1 g of active substance premix contains, for example, 1 mg of a compound according to the invention and 0.999 g of corn starch.

Example 16

Feed concentrate for cattle

| | |
|---|---|
| Shredded sugar beet | 600.0 g/kg |
| Maize gluten | 100.0 g/kg |
| Malted germs | 50.0 g/kg |
| Soya-bean flour | 35.0 g/kg |
| Wheat | 119.0 g/kg |
| Molasses | 60.0 g/kg |
| Edible phosphates | 12.0 g/kg |
| Calcium carbonate | 2.5 g/kg |
| Salt | 5.0 g/kg |
| Minerals | 10.0 g/kg |
| Vitamin premix | 5.5 g/kg |
| Active substance premix | 1.0 g/kg |

These components, when carefully mixed in the quantities specified, produce 1 kg of feed.

The 1 g of active substance premix contains for example 2 mg of a compound according to the invention and 0.998 g of corn starch.

Example 17

Fattening feed for lambs

| | |
|---|---|
| Barley | 690 g/kg |
| Soya-bean flour | 100 g/kg |
| Maize | 159 g/kg |
| Molasses | 30 g/kg |
| Vitamin/mineral mixture | 20 g/kg |
| Active substance premix | 1 g/kg |

These components, when carefully mixed in the quantities specified, produce 1 kg of feed.

The 1 g of active substance premix contains for example 2 mg of active substance and 0.998 g of corn starch.

What we claim is:

1. A phenylethanolamine of formula

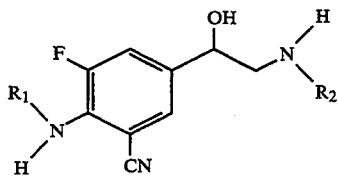

wherein
R₁ is hydrogen, or a carbonyl group substituted by C₁-C₄ alkoxy
R₂ is a group of formula

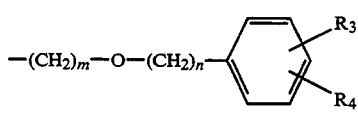

wherein
m is an integer from 2 to 8,
n is an integer from 1 to 7,
R₃ and R₄, which may be identical or different, are hydrogen, fluoro, chloro, bromo, methyl, ethyl, hydroxy, methoxy or ethoxy or
R₃ and R₄ together are methylenedioxy or ethylenedioxy or a pharmaceutically acceptable acid addition salt thereof.

2. The phenylethanolamine as recited in claim 1, wherein
R₁ is hydrogen, methoxycarbonyl or ethoxycarbonyl,
m is an integer 5, 6 or 7,
n is an integer 3, 4, or 5,
R₃ is hydrogen, hydroxy or methoxy, and
R₄ is hydrogen or a pharmaceutically acceptable acid addition salt thereof.

3. 1-(4-ethoxycarbonylamino-3-cyano-5-fluoro-phenyl)-2-[6-(4-phenylbutoxy)hexylamino]-ethanol or a pharmaceutically acceptable acid addition salt thereof.

4. 1-(4-amino-3-cyano-5-fluoro-phenyl)-2-[6-(4-phenylbutoxy)-hexylamino]-ethanol or a pharmaceutically acceptable acid addition salt thereof.

5. A pharmaceutical composition of matter comprising a phenylethanolamine as recited in claim 1 together with one or more inert carriers or diluents.

6. A method for treating bronchospasm in a warm-blooded animal which comprises administering to said animal a therapeutically effective amount of a phenylethanolamine as recited in claim 1.

* * * * *